United States Patent
Tal (10) Patent No.: US 7,182,755 B2
(45) Date of Patent: Feb. 27, 2007

(54) METHOD AND APPARATUS FOR TREATMENT OF THROMBOSED HEMODIALYSIS ACCESS GRAFTS

(75) Inventor: Michael G. Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 100 days.

(21) Appl. No.: 10/947,423

(22) Filed: Sep. 23, 2004

(65) Prior Publication Data

US 2005/0065469 A1    Mar. 24, 2005

Related U.S. Application Data

(60) Provisional application No. 60/505,665, filed on Sep. 24, 2003.

(51) Int. Cl.
*A61M 31/00* (2006.01)
*A61M 29/00* (2006.01)

(52) U.S. Cl. ............ 604/507; 604/509; 604/96.01

(58) Field of Classification Search ........ 604/500, 604/506–510, 93.01, 95.03, 96.01, 99.04, 604/101.03, 101.04, 102.01, 102.03, 912, 604/915; 606/191, 192, 194

See application file for complete search history.

(56) References Cited

U.S. PATENT DOCUMENTS

| | | | | |
|---|---|---|---|---|
| 5,085,635 A | * | 2/1992 | Cragg | ............ 604/102.03 |
| 5,665,063 A | | 9/1997 | Roth et al. | |
| 5,766,191 A | * | 6/1998 | Trerotola | ............ 606/159 |
| 5,779,673 A | | 7/1998 | Roth et al. | |
| 6,063,069 A | * | 5/2000 | Cragg et al. | ............ 604/508 |
| 6,146,396 A | | 11/2000 | Konya et al. | |
| 6,569,146 B1 | | 5/2003 | Werner et al. | |
| 6,602,264 B1 | * | 8/2003 | McGuckin, Jr. | ............ 606/159 |
| 6,622,364 B2 | | 9/2003 | Bolduc et al. | |
| 6,663,613 B1 | * | 12/2003 | Evans et al. | ............ 604/523 |
| 2002/0029073 A1 | * | 3/2002 | Schwartz | ............ 607/105 |
| 2002/0062119 A1 | | 5/2002 | Zadno-Azizi | |
| 2002/0188276 A1 | | 12/2002 | Evans et al. | |
| 2003/0104073 A1 | | 6/2003 | Johansson et al. | |
| 2003/0139751 A1 | | 7/2003 | Evans et al. | |
| 2004/0006306 A1 | | 1/2004 | Evans et al. | |
| 2004/0097880 A1 | | 5/2004 | Schur | |
| 2005/0113800 A1 | * | 5/2005 | Schur | ............ 604/510 |

* cited by examiner

*Primary Examiner*—Catherine S. Williams
(74) *Attorney, Agent, or Firm*—Welsh & Flaxman LLC (57) ABSTRACT

A method for the treatment of thrombosed hemodialysis access grafts or fistulas defining a shunt positioned between an arterial side and a venous side is achieved by inserting a balloon catheter within the shunt, wherein the balloon catheter includes a distal balloon and at least one infusion aperture located proximally of the distal balloon. Thereafter, the balloon catheter is advanced within an arterial anastomosis at an artery-shunt juncture and the distal balloon is inflated. A thrombolytic agent is then injected through the infusion apertures of the balloon catheter into the shunt to chemically destroy clot material within the shunt, whereby applying the thrombolytic agent with the distal balloon inflated at the arterial anastomosis the possibility of the clot material moving into the artery is prevented and there is no need to worry about the migration of the clot into the arterial system and the resulting complications. Finally, the inflated distal balloon is pulled toward the venous side, eradicating the arterial plug. A balloon catheter for use in accordance with the present invention is also disclosed.

12 Claims, 12 Drawing Sheets

METHOD AND APPARATUS FOR TREATMENT OF THROMBOSED HEMODIALYSIS ACCESS GRAFTS

CROSS REFERENCE TO RELATED APPLICATIONS

This application is based upon U.S. Provisional Patent Application Ser. No. 60/505,665, filed Sep. 24, 2003, entitled "Dialysis Access Thrombectomy Catheter".

BACKGROUND OF THE INVENTION

1. Field of the Invention

The present invention relates to the field of interventional radiology. More particularly, the invention relates to a method and apparatus for the reconstruction of a flow path within a vascular conduit. The invention further relates to embolectomy and thrombectomy, including treatment of thrombosed hemodialysis access grafts or fistulas.

2. Description of the Prior Art

Life-sustaining access to hemodialysis is one of the leading causes for hospital admission. More than 80% of the patient population undergoing hemodialysis treatments have a PTFE graft access. However, PTFE graft access only offers an average patency of 20 months after placement.

If one considers that the arterial and venous anatomy is typically sufficient to support three upper extremity grafts, a dialysis patient may expect an average 10 years of permanent access availability from upper extremities; that is, 20 months times six potential grafts. Depending on the age when the kidneys fail, between 23% and 51% of patients will live at least 10 additional years after starting dialysis. If a renal transplant does not become available, many patients will need to resort to peritoneal dialysis or a less preferable hemodialysis access such as a lower extremity graft or a hemodialysis catheter. Some patients may even die because of lack of access. Therefore, efforts to maintain each available permanent hemodialysis access have become a matter of paramount importance.

Thrombosis, or blood clot formation, is the most common cause of hemodialysis access graft failure. Graft thrombosis usually results from venous flow obstruction, or stenosis. The location of the stenosis is most commonly found at the graft-vein anastomosis. A narrowing at this area causes a slow down or obstruction of blood flow, resulting in the formation of the thrombus within the graft. Venous stenosis is present in over eighty-five percent of clotted grafts. The underlying venous anastamotic stenosis must be corrected in order to avoid recurrence of the thrombus.

There are at least three primary interventional radiology methods for percutaneous thrombolysis: Thrombolytic (rolkinase, stereptokinase, Tissue plasminogen activator (TPA, r-TPA), and other) infusion, pulse-spray pharmacomechanical thrombolysis, and pure mechanical thrombolysis.

Percutaneous thrombolysis is the least invasive treatment option for graft treatment and has rapidly become the preferred method of treatment at most institutions. It is commonly accomplished using mechanical thrombectomy devices that macerate the clot or by using a thrombolytic agent to dissolve the clot. Mechanical thrombectomy devices are expensive and often require capital investment. Thrombolytic agents provide a less expensive treatment option.

Tissue plasminogen activators, also known as TPA, are one of the most commonly used thrombolytic agents for clearing dialysis grafts. The drug is introduced into the clotted graft via an infusion catheter or a needle. TPA has a high affinity and specificity for fibrin, a major component of blood clots. It acts upon the clot by binding to the surface and dissolving it by an enzymatic reaction. The time until clot dissolution is dependent on the length and size of the clot, the amount of drug delivered and method used for drug delivery.

With the "lyse and wait" technique of thrombolysis, TPA or other thrombolytic agent, such as, urokinase or retaplase, is delivered to the graft by a small gauge needle or an infusion catheter. Manual compression is applied to the graft-artery anastomosis during drug administration to ensure targeted drug delivery is restricted to the graft and prevent inadvertent dislodgment of clot into the artery. The procedure is performed without the aid of fluoroscopic guidance. The therapeutic action of the lytic agent typically takes at least one hour depending on the effective distribution of the lytic agent. After clot dissolution, the patient typically is brought into the angiographic suite for fluoroscopic imaging of the graft to identify and visualize residual venous stenosis. Angioplasty of the stenosed segment can then be performed.

With regard to mechanical thrombolysis, several devices are known to have been used. For example, a rotating nitinol basket-like fragmentation cage (Arrow-Trerotola Percutaneous Thrombolytic Device) has been used by crossing 5-F sheaths within a graft and requires only a minute or two to restore flow. In a recent study, fifty-one consecutive patients were treated with the device. In all patients, the device was used to also treat the arterial plug in situ at the arterial anastomosis instead of using a Fogarty catheter to reposition the plug as indicated by the product labeling of the devices. Immediate technical patency was 100% with 6% arterial embolization vs. 2% control. Adjunctive therapy with a Fogarty Adherent Clot catheter was needed in two procedures (4%).

The Amplatz mechanical thrombectomy device (Clot Buster, Microvena Co.), has also been used successfully in dialysis grafts. This 8-French device consists of a gas-driven, high-speed (150,000 rpm) cam that pulverizes the clot. In a randomized series comparing surgical thrombectomy with the device, 89% success was achieved in the device group and 83% in the surgery group. Thirty-day patency was lower with the device (47%) than with surgery (77%). However, residual thrombus may occur with the device, and it cannot be used to treat the arterial plug. Recently, the device has been made available also in a 6-French version. Because the device is not guidewire compatible, a 6-French ID or 8-French ID delivery sheath or an 8-French OD or 6-French OD guiding catheter should be used.

The Hydrolyser catheter (Cordis) uses the Venturi effect to achieve mechanical thrombolysis. The catheter is driven using a conventional angiographic injector. Although testing shows this device was successful in $15/16$ instances, five reclotted within 24 hours. Secondary patency was 41% at 6 months. One concern with this device, however, is the amount of blood aspirated during the procedure (50–150 mL), which could be problematic for chronically anemic patients.

The Cragg thrombolytic brush consists of a 6-French brush catheter, and combines mechanical thrombolysis with thrombolytics to shorten procedure time and reduce thrombolytic dose. It is not a purely mechanical thrombolytic approach, but it takes advantage of many principles of mechanical thrombolysis. This 6-French device consists of a nylon brush that rotates at low speed (1,800 rpm.) driven by a single-use detachable motor drive. It is not guidewire compatible. Another similar design is the Castaneda Over-the Wire Brush (MT1), which is more preferred because of its guidewire compatibility. The brush itself is modified and allows for using the system forward and backward.

U.S. Pat. No. 4,921,484 discloses a device that uses a tubular mesh in a mesh balloon catheter device. Although this design has shown some utility, it does not offer guidewire compatibility. Thus, it may be necessary to use an additional device(s) to steer toward a desired place within a vessel.

Among simpler devices, the Fogarty Arterial Embolectomy Catheter (Baxter Scientific Products, McGaw Park, Ill.) has shown some utility in removing arterial clots. Although the original Fogarty catheters were not guidewire compatible, guidewire compatible Fogarty balloons (Baxter) have recently been made available. Other over-the-wire alternatives include occlusion balloons and PTA balloons to macerate the clots. The basic technique for recanalization of hemodialysis access grafts using these devices often consists of a crossover catheterization requiring, unfortunately, multiple equipment. Specifically, two introducer sheaths and two balloon catheters are used. For dislodgment of an arterial plug or intragraft stenosis, the Fogarty Adherent Clot Catheter (Baxter) has been successfully used in some cases. Another similar alternative is the Fogarty Graft Thrombectomy Catheter (Baxter), which was designed to remove tough, mature thrombus from synthetic grafts. Except for the over-the-wire Fogarty balloon, the other designs have no guidewire compatibility.

Despite many advantages, traditional mechanical thrombolytic devices often exhibit significant drawbacks. Some devices are large (8-French or more) and perform poorly in curved vessels, limiting their use in hemodialysis access. Residual adherent clot is a considerable problem with some mechanical devices. Many devices do not remove the macerated clot and it may be embolized into the lungs. A great number of the available devices cannot be used over-the-wire.

Another method was recently described in which access is achieved toward the venous and arterial anastomosis and an occlusion balloon catheter is inflated at the arterial anastomosis site. While the balloon is inflated, a large quantity (approximately 40–60 cc) of saline is injected into the graft through the sheath, "washing" the residual clot away. The presence of the balloon is "protecting" the artery from embolization of clot into it, a major and infrequent complication. The occlusion balloon is then inflated in the arterial anastomosis site or adjacent to it. Again, infusion of saline or contrast material or thrombolytic drugs can be injected. The technique is working very well, however, the whole length of the graft cannot be cleared or visualized.

With the foregoing apparatuses in mind, a preferred current technique for comprehensive shunt cleansing begins with inserting a needle through the skin and into the shunt. A small wire is then inserted through the needle and the tactile sensation transmitted by the wire is used in determining whether the wire is in the shunt. The skin site is then inspected with X-ray to determine the position of the wire and whether it is within the shunt, the needle is removed when the wire is determined to be in the shunt interior, a small catheter is placed over wire with the discharge orifice within the shunt and the wire is removed leaving the catheter with its discharge end within the shunt.

The larger wire is then inserted through the catheter into the shunt interior and the catheter is removed. The next step involves inserting a sheath over the larger wire and into the shunt. A balloon catheter is then advanced into the venous anastomosis and the balloon is inflated to crush the venous anastomosis and open the shunt-vein juncture. Thereafter, the balloon and wire are removed, a second sheath is inserted between the position of the first sheath insertion and shunt-vein juncture, into a clean shunt region, and the clot is macerated and eradicated either mechanically or pharmacologically.

A balloon is then pushed into position within arterial anastomosis at the artery-shunt juncture and the balloon is inflated and pulled back, eradicating the arterial plug and removing the platelet plug and residual arterial anastomosis from the shunt-artery juncture by pulling on the balloon.

Unfortunately, injection of a contrast material into the graft cannot be safely performed before flow in the graft is reestablished. In some cases, flow cannot be established and the operator cannot tell what is the cause for the lack of success. After flow is reestablished, the operator may eradicate additional visualized stenosis. The final step is that of removing the balloon, wire and the sheath.

As those skilled in the art will appreciate, the prior art techniques relating to the treatment of a thrombosed hemodialysis access graft or fistula exhibit various shortcomings. In particular, current techniques offer no mechanism for the application of thrombolytic solutions and contrast solutions within the occluded graft due to concerns relating to the migration of clots into the arterial system. As such, thrombolysis and imaging of the graft must be achieved utilizing additional steps and procedures. This is undesirable. The present invention overcomes the shortcomings of the prior art by providing an effective and reliable method and apparatus for the reconstruction of a flow path within a vascular conduit. It also provides a way to safely inject contrast material and thrombolytic drugs into an occluded graft prior to restoration of flow.

SUMMARY OF THE INVENTION

It is, therefore, an object of the present invention to provide a method for the treatment of thrombosed hemodialysis access grafts or fistulas defining a shunt positioned between an arterial side and a venous side. The method is achieved by inserting a balloon catheter within the shunt, wherein the balloon catheter includes a distal balloon and at least one infusion aperture located proximally of the distal balloon. Thereafter, the balloon catheter is advanced within an arterial anastomosis at an artery-shunt juncture and the distal balloon is inflated. A thrombolytic agent is then injected through the infusion aperture of the balloon catheter into the shunt to chemically destroy clot material within the shunt, wherein by applying the thrombolytic agent with the distal balloon inflated at the arterial anastomosis the possibility of the clot material moving into the artery is prevented and there is no need to worry about the migration of the clot into the arterial system and the resulting complications. Finally, the inflated distal balloon is pulled toward the venous side, eradicating the arterial plug.

It is also an object of the present invention to provide a balloon catheter including a catheter body with a compliant balloon secured at a distal end of the catheter body, a plurality of apertures positioned proximally of the balloon, wherein the plurality of apertures are positioned on diametrically opposed sides of the catheter body, a first lumen extending through the catheter body and in fluid communication with the balloon for selectively inflating and deflating the balloon, and a second lumen extending through the catheter body and in fluid communication with the apertures for dispensing solution therethrough.

It is another object of the present invention to provide a balloon catheter including a catheter body with a compliant balloon secured at a distal end of the catheter body, a single aperture positioned proximally of the balloon, a first lumen extending through the catheter body and in fluid communication with the balloon for selectively inflating and deflating the balloon, and a second lumen extending through the catheter body and in fluid communication with the aperture for dispensing solution therethrough.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

With reference to FIGS. 1, 2, 3a and 3b, a balloon catheter 10 with proximal infusion apertures 12 for the injection of thrombolytic agents or contrast materials is disclosed. The present balloon catheter 10 is preferably designed for use in dialysis access declotting, although those skilled in the art will appreciate that it may be used for a variety of applications. In accordance with a preferred embodiment of the present invention, the catheter 10 is approximately 40 cm to approximately 60 cm long, although those skilled in the art will appreciate that other lengths may be used without departing from the spirit of the present invention.

Figure 1:
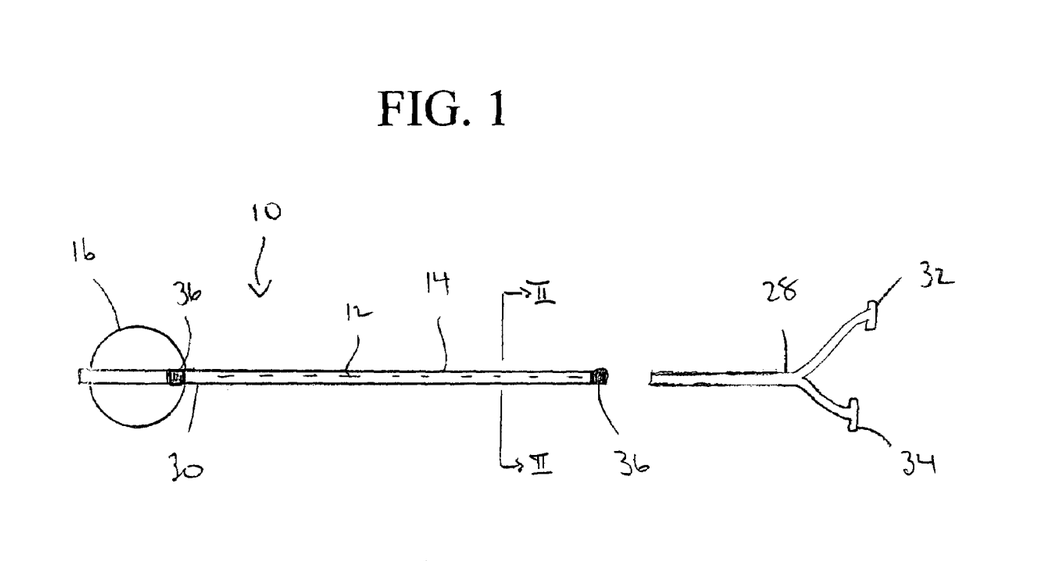
FIG. 1 is a side view of a balloon catheter in accordance with the present invention.

More particularly, the balloon catheter 10 includes a longitudinally extending catheter body 14 having a distal balloon 16 formed thereon. The distal balloon 16 is formed over the catheter body 14 in a traditional manner and is shaped and dimensioned to substantially seal an arterial anastomosis 48 as discussed below. It is important to understand that the distal balloon 16 must be occluding the arterial anastomosis 48 prior to injection of thrombolytics or contrast materials. If by mistake the distal balloon 16 is inflated at the venous anastomotic site, the result would be migration of clot into the artery and arterial embolization, the exact complication we aim to prevent with this invention.

As discussed below, the balloon 16 is not used for dilatation purposes and is formed to function as an occlusion balloon. With this in mind, the distal balloon 16 is constructed to be highly compliant and may be composed of one or more layers of expandable material, such as, polyurethane, radiopaque polyurethane material, thermoplastic polyurethane elastomers, aliphatic polyurethanes, aromatic polyurethanes, styrene-ethylene-butylene-styrene (SEBS) block copolymer, thermoplastic elastomers, low-density polyethylene, polyethylene terephthalate, polyethylene terephthalate glycol, silicone, copolymer of polyurethane and silicone, natural rubber, synthetic rubber, thermoplastic polyamide, nylon, latex, polyethylene, polyisoprene, polyisobutylene, thermoplastic elastomers, an elastomeric material, or combinations thereof. Occlusion balloons are well known in the art and those skilled in the art will appreciate the various constructions that may be used in accordance with the present invention.

Proximal to the distal balloon 16 are a series of infusion apertures 12 through which thrombolytic agent 18 or contrast material 22 is delivered to the treatment site 20 in a manner discussed below in greater detail. In accordance with a preferred embodiment, the plurality of infusion apertures 12 are positioned along the length of the catheter body such that they are diametrically opposed, as it is believed this orientation will result in the best performance. However, it is also contemplated the infusion apertures may be formed about the circumference of the catheter body or in other arrangements those skilled in the art may see fit to employ.

The infusion apertures 12 may be formed as circular holes (see FIG. 3b) or longitudinally extending slots (see FIG. 3a), and similar reference numerals are used for both. It is contemplated the slots (see FIG. 3a) may be approximately 1 mm to approximately 1 cm in length. In accordance with a preferred embodiment of the present invention, the infusion apertures 12, whether they be slots or circular holes, are relatively small for creating pressure during the application of the thrombolytic agent 18. In fact, the infusion apertures 12 may be formed in such a way that they are substantially closed until such a time that adequate pressure is applied for opening the infusion apertures 12 and permitting the thrombolytic agent 18 (or contrast material 22 or other solution) to be sprayed therefrom at a relatively high pressure. The spraying of the thrombolytic agent 18 in this way creates a mechanical cleansing action that complements the chemical action of the thrombolytic agent 18. A variety of thrombolytic agents are known to those skilled in the art and various thrombolytic agents may be employed without departing from the spirit of the present invention.

Figure 4:
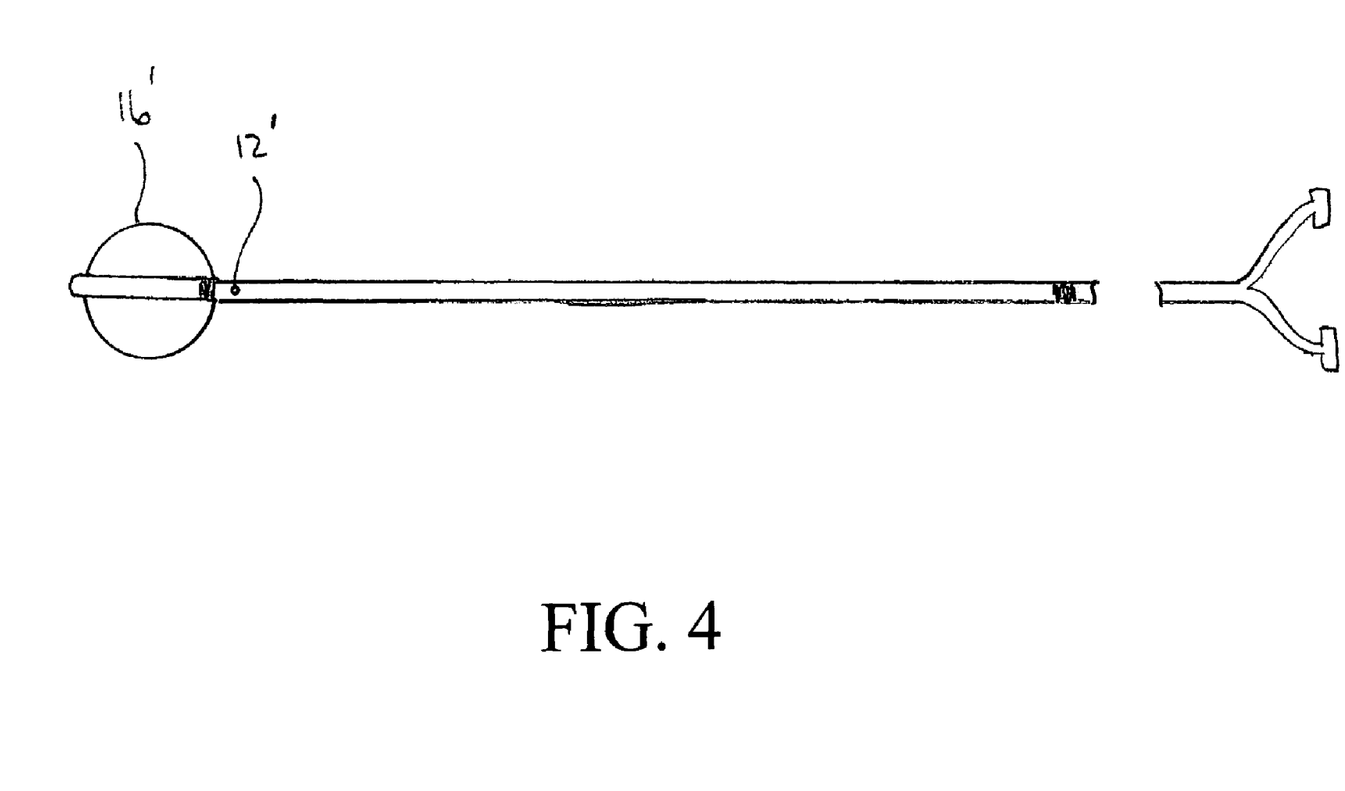
FIG. 4 is a side view of a balloon catheter in accordance with an alternate embodiment that employs a single aperture just proximally of the balloon catheter.

While a plurality of infusion apertures are disclosed in accordance with a preferred embodiment of the present invention, the balloon catheter 10' may be constructed with a single infusion aperture 12' without departing from the spirit of the present invention (see FIG. 4). In fact, it has been found that a single infusion aperture 12' proximal to and adjacent the distal balloon 16' results in ideal imaging characteristics. In accordance with a preferred embodiment, the single infusion aperture 12' should be positioned as close to the distal balloon 16' as reasonably possible. The positioning of the infusion aperture 12' just proximally of the distal balloon 16' results in a flow of contrast material that makes imaging with the present balloon catheter 10' highly effective. More specifically, by positioning the single infusion aperture 12' just proximally of the distal balloon 16', the contrast material is able to opacify the entire graft 42 with a single injection of contrast material.

Figure 2:
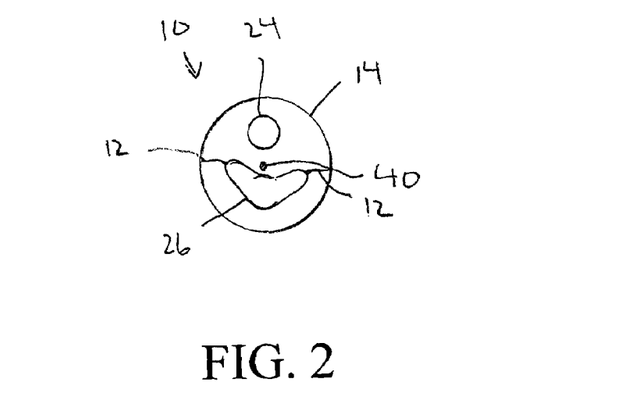
FIG. 2 is a cross sectional view of a balloon catheter shown in FIG. 1 along the line II—II.

In accordance with a preferred embodiment of the present invention, and with reference to FIGS. 1 and 2, the catheter body 14 includes at least two lumens 24, 26 respectively maintaining fluid communication between the proximal end 28 of the catheter body 14 and the distal end 30 of the catheter body 14 where the infusion apertures 12 and distal balloon 16 are positioned. The first lumen 24 is maintained in fluid communication with the interior of the distal balloon 16 allowing the balloon 16 to be inflated and deflated under the control of a syringe (not shown) coupled to the first lumen 24 via a port 32 located at the distal end of the first lumen 24. The first lumen 24 must be shaped and dimensioned to permit the free flow of an inflation medium during inflation and deflation of the distal balloon 16. The second lumen 26 is maintained in fluid communication with the series of infusion apertures 12 located proximally of the distal balloon 16. The second lumen 26 allows for the passage of fluids through the catheter body 14 for passage through the series of the infusion apertures 12 at predetermined treatment sites. As with the first lumen 24, the second lumen 26 is provided with a port 34 at its distal end for the application of the thrombolytic agent 18, contrast material 22 and other solutions. As with the first lumen 24, the second lumen 26 must be shaped and dimensioned to permit the free flow of thrombolytics, contrast materials and other solutions to the infusion apertures 12.

Figure 2A:
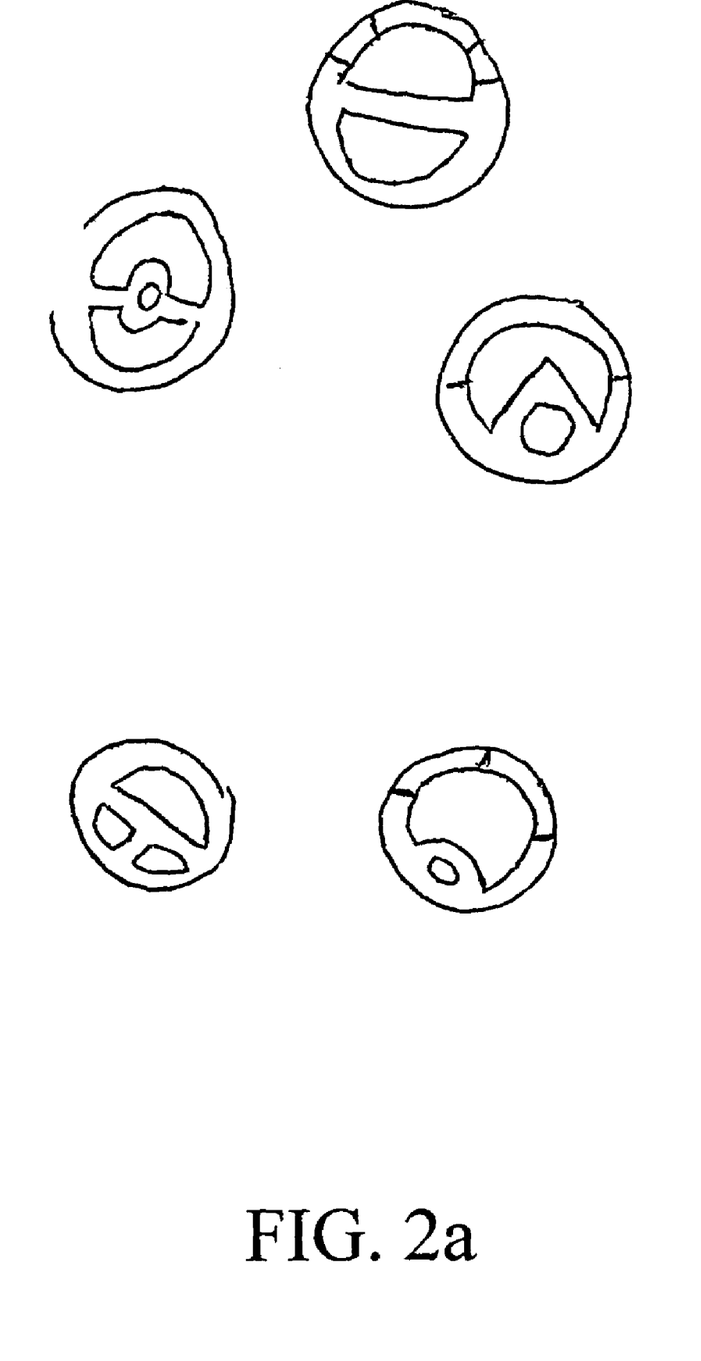
FIG. 2a shows various alternate cross sectional profiles that may be used in accordance with the present invention.
Figure 3A:
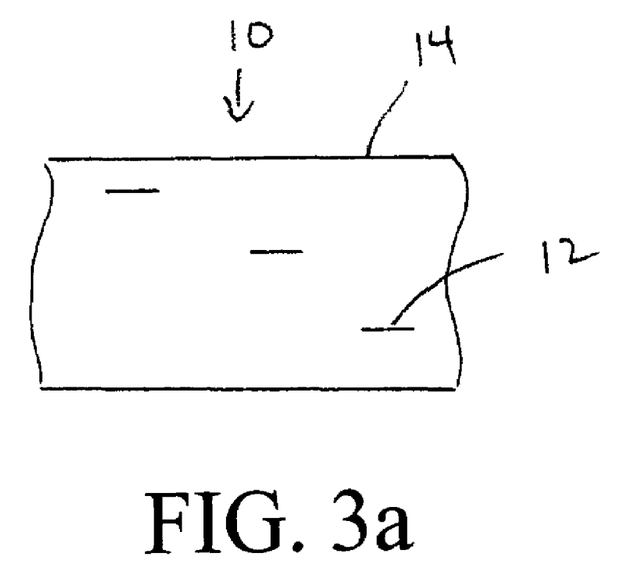
FIGS. 3a and 3b are detailed views of various embodiments showing the aperture shapes.
Figure 3B:
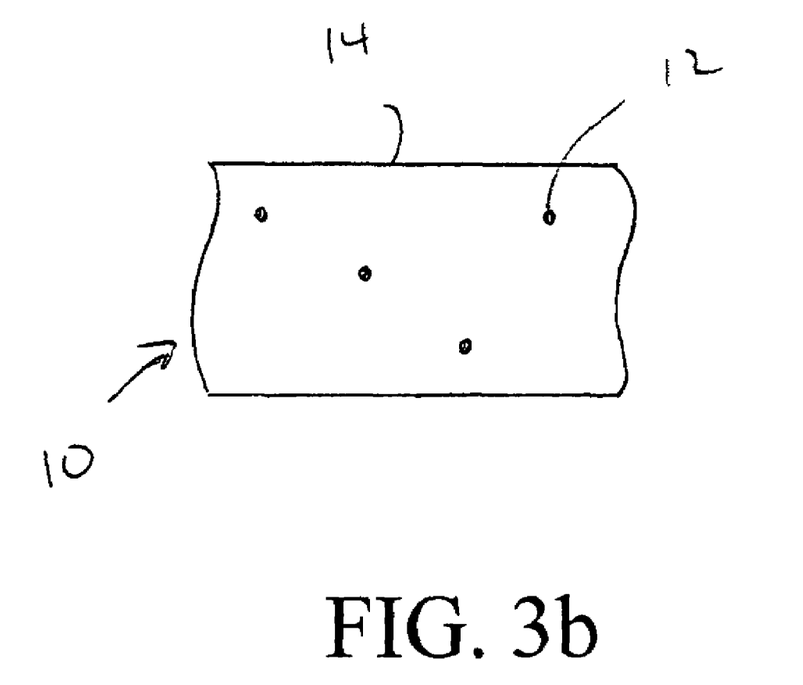
Figure 5:
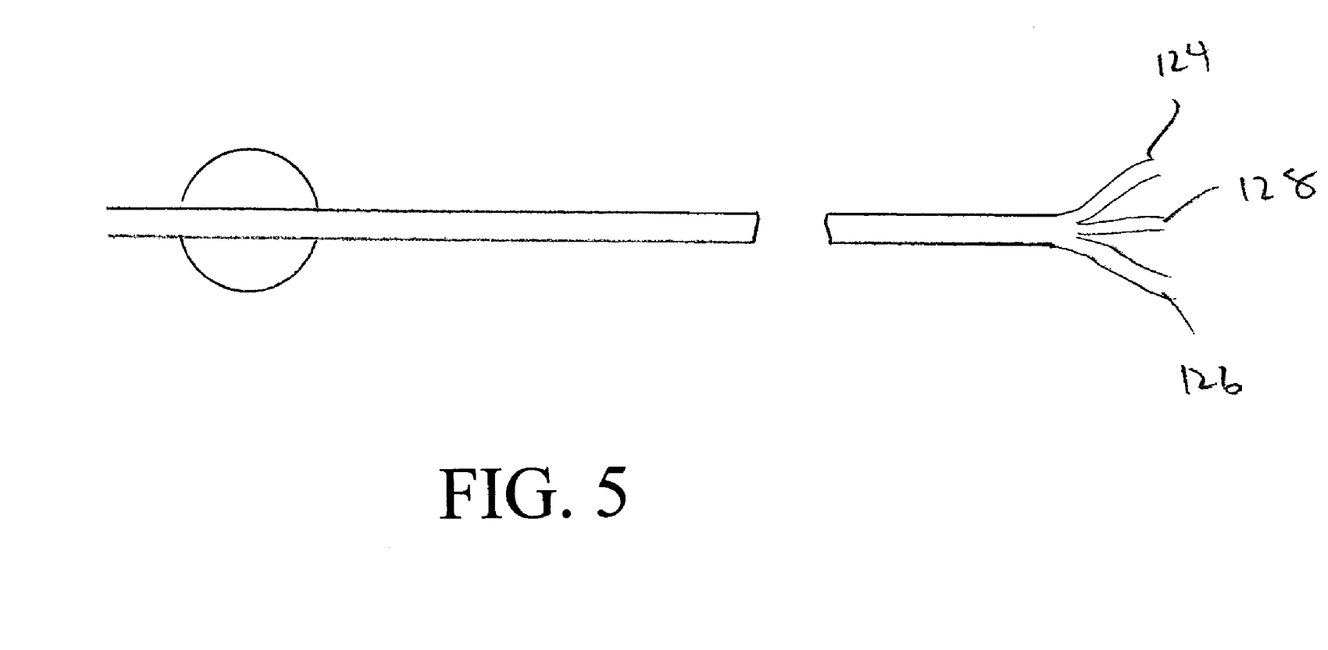
FIG. 5 is a side view of a balloon catheter in accordance with the present invention including a third lumen.
Figure 6:
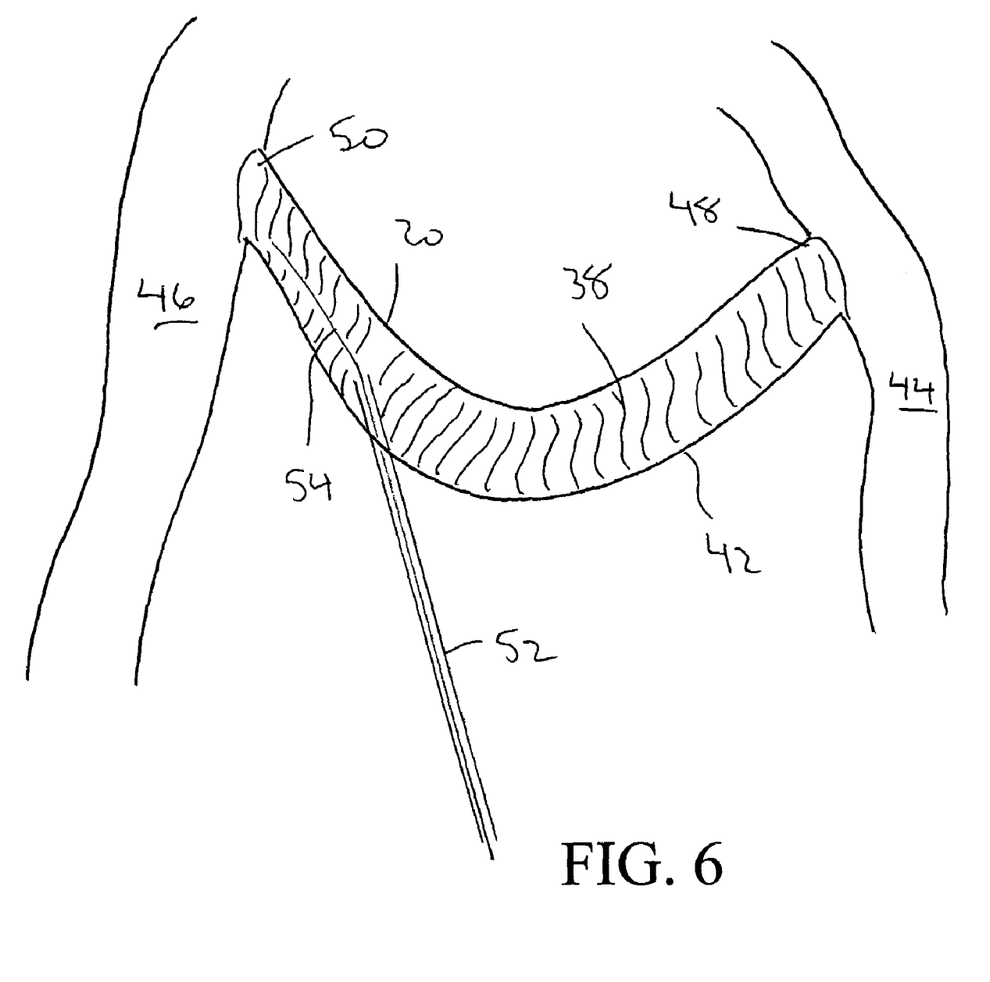
FIGS. 6 to 12 show the steps associated with treatment of thrombosed hemodialysis access grafts or fistulas in accordance with the present invention.
Figure 7:
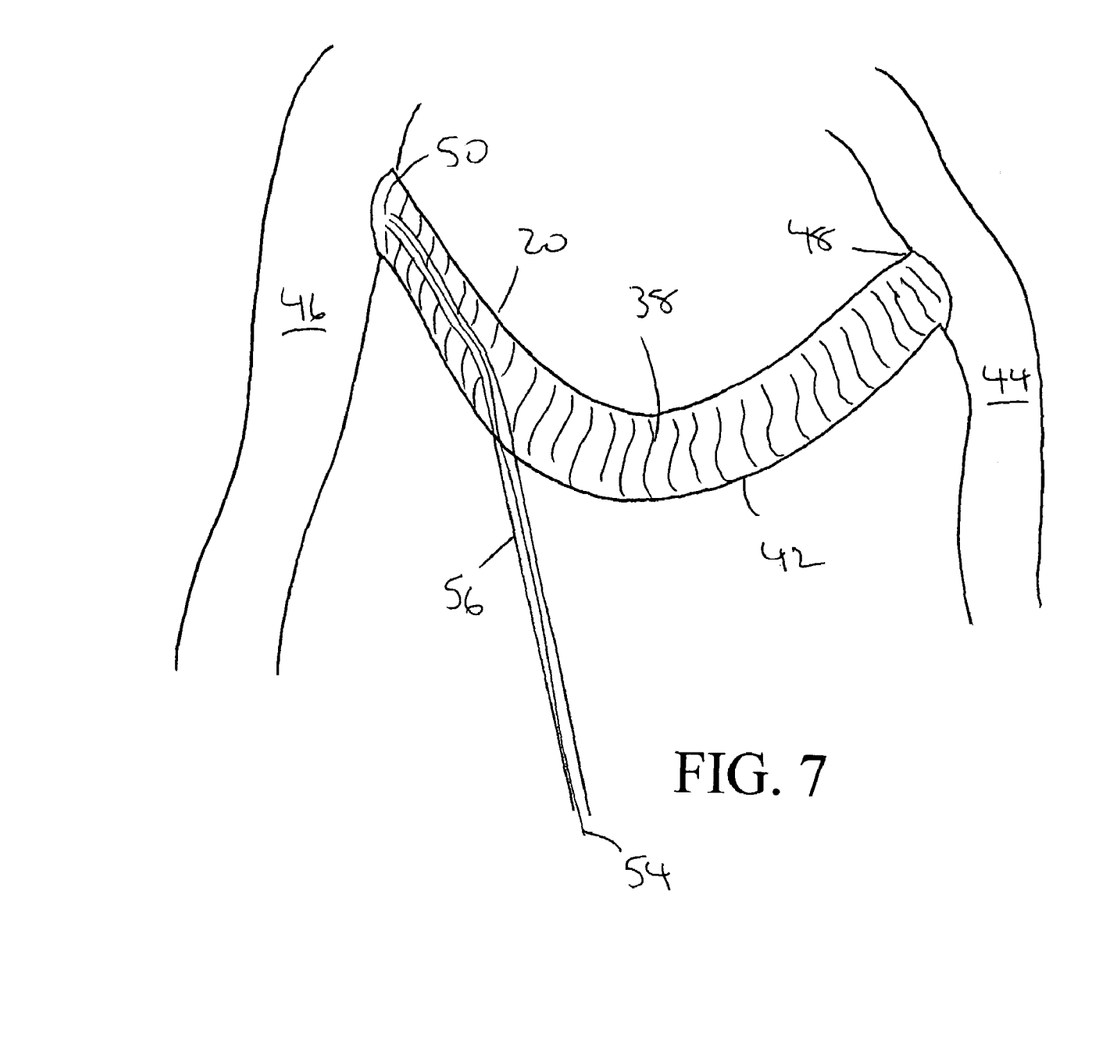
Figure 8:
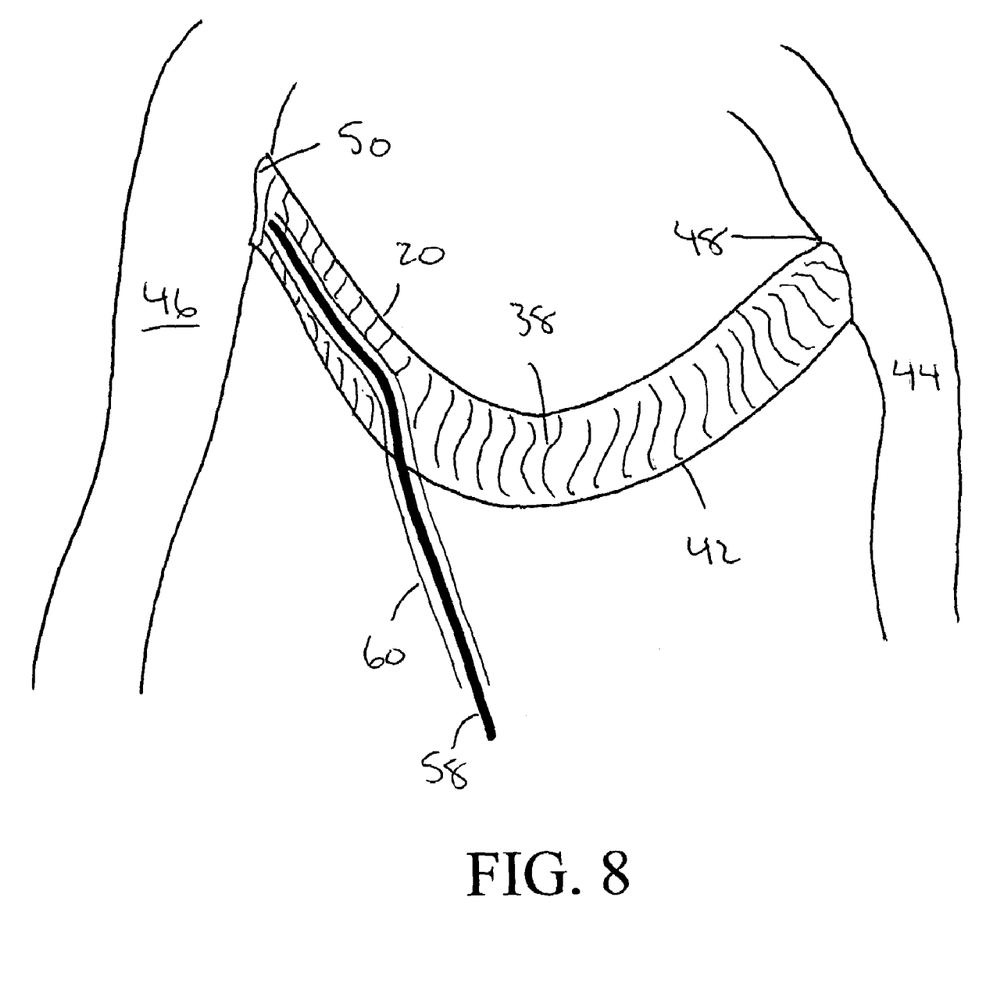
Figure 9:
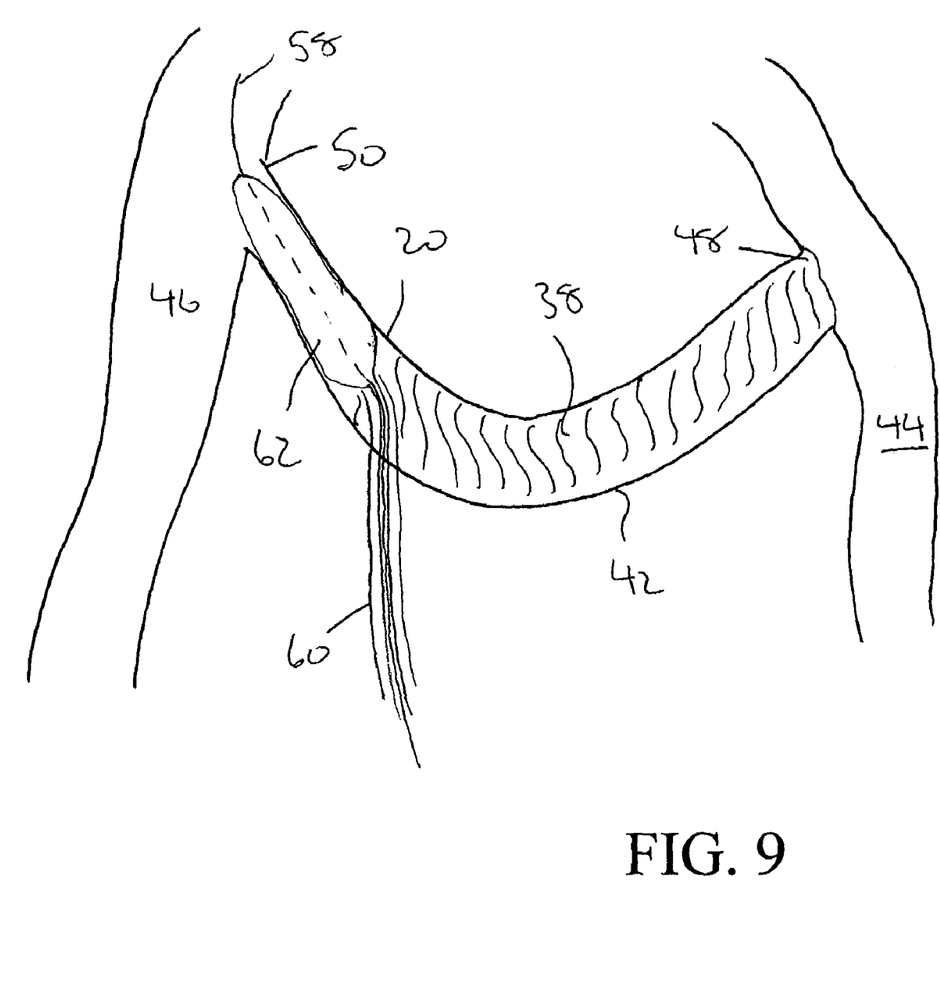

While a specific balloon catheter construction is disclosed above in accordance with a preferred embodiment of the present invention, variations on the balloon catheter construction may be employed without departing from the spirit of the present invention. For example, the balloon catheter may be constructed as an over the wire (0.018–0.038") balloon catheter and, therefore, be constructed with three lumens 124, 126, 128 (see FIG. 5). In addition, although an exemplary cross sectional profile of the two lumen balloon catheter 10 of FIG. 1 is shown in FIG. 2, a wide variety of cross section profiles may be employed in accordance with the embodiments of FIGS. 1 and 2 without departing from the spirit of the present invention. Exemplary alternate cross sectional profiles are shown in FIG. 2*a*.

Radiopaque markers 36 are also positioned at either end of the treatment region. The structure of catheter 10 is advantageous in that it will completely contain the thrombolytic agent 18 and all disrupted clot material 38 proximally of the distal balloon 16. Aspiration means may also be provided, e.g., through an additional lumen within the catheter body 14, in order to withdraw materials from the treatment region.

The catheter body 14 may also be provided with a longitudinally extending stiffener rod 40. As those skilled in the art will certainly appreciate, the stiffener rod 40 will assist the medical practitioner in maneuvering the present catheter 10 through the vascular system.

Figure 10:
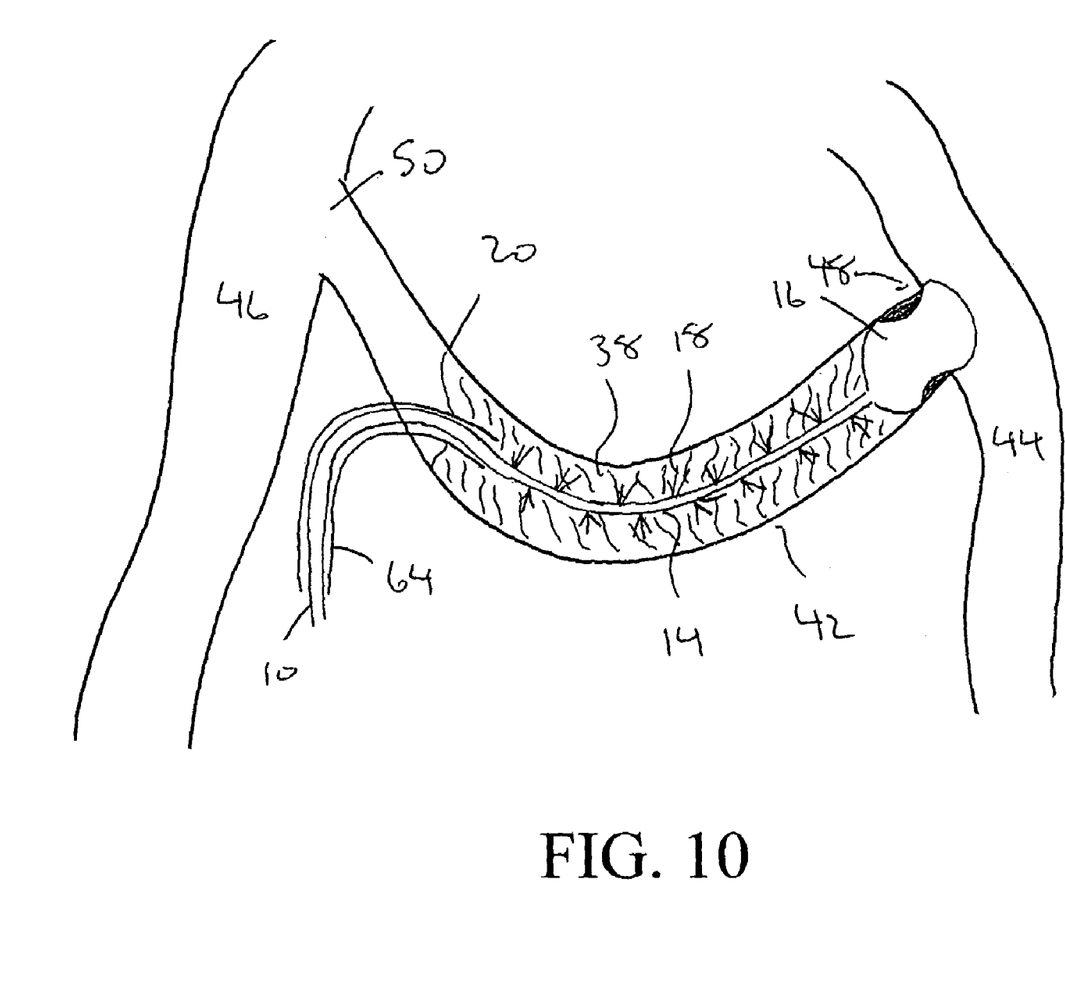
Figure 11:
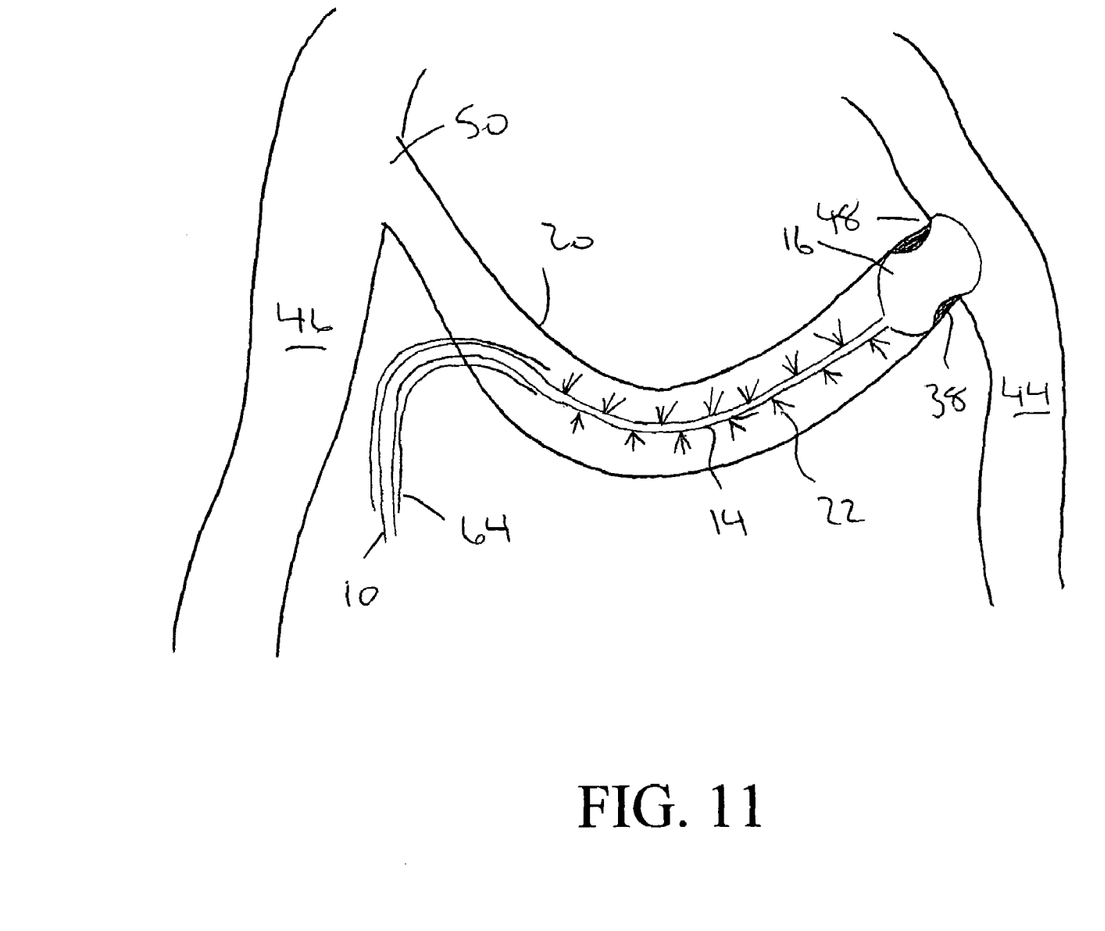
Figure 12:
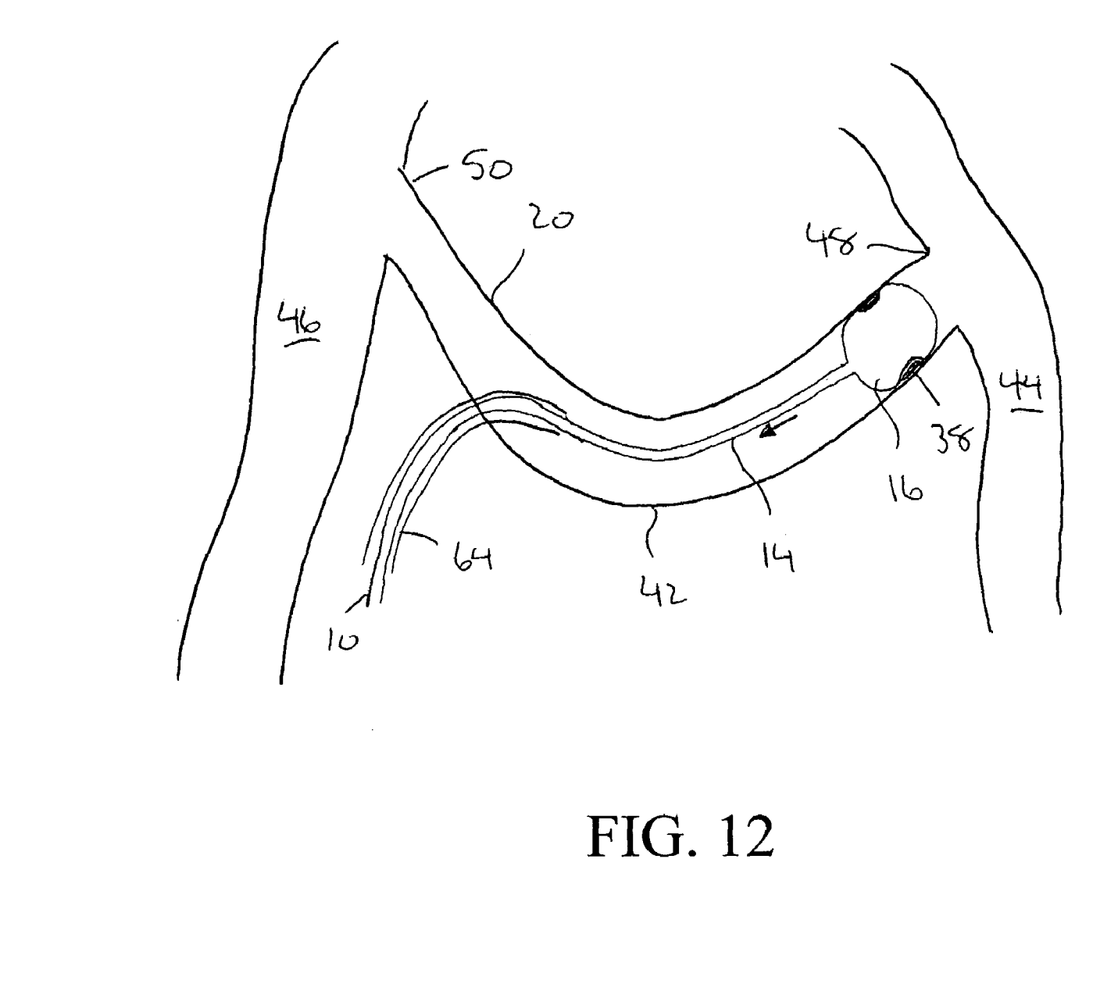

As will be discussed below in greater detail, the present balloon catheter 10 is designed for performing various functions during dialysis access (graft or fistula) procedures. For example, the balloon catheter 10 is designed for injecting thrombolytic agents 18 into a graft 42 or fistula, either via pulse-spray or by instillation (see FIG. 10). This is accomplished with the balloon 16 inflated (if the catheter 10 is directed towards the arterial side 44 of the shunt 20 as shown in FIG. 10) or with the balloon 16 deflated (if the catheter 10 is directed toward the venous side 46 of the shunt 20). The balloon catheter 10 is also adapted for imaging of the graft during thrombolysis or mechanical thrombectomy and visualization of any residual clot. This is accomplished by injecting a contrast material 22 while the balloon 16 is inflated along the arterial side 44 of the shunt 20 (see FIG. 11). As those skilled in the art will appreciate, no current technique offers a mechanism for visualizing the graft prior to reestablishment of flow. The balloon catheter 10 is further adapted for flushing a clot 38 from the graft 42 to reestablish flow. This is accomplished by inflating the balloon 16 in the graft 42 adjacent to the arterial anastomosis 48 and pumping a volume of saline (approximately 30–60 cc) into the graft 42.

When flow is restored in the graft 42, the balloon catheter 10 may also assist in imaging of the whole graft 42, including the arterial anastomosis 48 with a single injection. This is achieved by inflating the balloon 16 at the venous anastomosis 50 and applying a contrast material through the infusion apertures 12. Through the utilization of this technique there is no need to occlude the graft with a Kelley clamp, operator finger or with an angioplasty balloon. Techniques such as those described above can be used with the venous anastomosis and angioplasty procedures, in addition to thrombectomy/lysis.

As those skilled in the art will appreciate, the present balloon catheter 10, when employed in accordance with the procedure outlined below will replace the Fogerty thrombectomy balloon and Cragg-MacNamara or Angiodynamics multi-side hole infusion catheters. The balloon catheter 10 advantageously allows for a rapid clot removal procedure with visualization of the graft 42 and working environment, replaces dual catheters employed in accordance with the prior art techniques with a single catheter and makes the procedure safer for the operators. Although those skilled in the art will appreciate a variety of uses for the present balloon catheter 10, the balloon catheter 10 is preferably used for thrombolytic declotting (TPA, rTPA and Urokinase) and mechanical declotting, whether with the Angiojet, Trerotola, or any other mechanical thrombectomy devices.

With reference to FIGS. 6 to 12, and in accordance with a preferred embodiment of the present invention, the present shunt cleansing procedure begins with the insertion of a needle 52 through the skin and into the shunt 20. Next, a small wire 54 is inserted through the needle 54, tactile sensation transmitted by the wire 54 is employed in determining whether the wire 54 is in the shunt 20 and the skin site is inspected with X-ray to determine the position of the wire 54 and whether it is within the shunt 20.

The needle 52 is then removed when the wire 54 is determined to be in the shunt 20 interior and a small catheter 56 is placed over wire 54 with the discharge orifice within the shunt 20. The wire 54 is then removed.

After the wire 54 is removed, a larger wire 58 is inserted through the catheter 56 into the shunt 20 interior, the catheter 56 is removed and a sheath 60 is inserted over the larger wire 58 and into the shunt 20. A dilatation balloon catheter 62 is then advanced into the venous anastomosis 50 and the balloon catheter 62 is inflated to crush the venous anastomosis 50 and open the shunt-vein juncture. The balloon catheter 62 and wire 58 are then removed and a second sheath 64 is inserted between the first sheath 60 insertion and the shunt-vein juncture into a clean shunt region.

Thereafter, a thrombectomy balloon catheter 10 in accordance with the present invention as disclosed with reference to FIGS. 1, 2, 3*a* and 3*b* is pushed into position within arterial anastomosis 48 at the artery-shunt juncture and the distal balloon 16 is inflated to substantially seal the arterial anastomosis 48. As discussed above, it is important to understand that the distal balloon 16 must be occluding the arterial anastomosis 48 prior to injection of thrombolytics or contrast materials. If by mistake the distal balloon 16 is inflated at the venous anastomotic site, the result would be migration of clot into the artery and arterial embolization, the exact complication we aim to prevent with this invention. A thrombolytic agent 18 is then injected through the second lumen 26 and the infusion apertures 12. The thrombolytic agent 18 chemically destroys the clot 38 while the force of the spray created by the application of the thrombolytic agent 18 through the infusion apertures 12 mechanically disrupts the clot 18. By applying the thrombolytic agent 18 with the distal balloon 16 inflated at the arterial anastomosis 48, the possibility of the clot 38 moving into the artery is prevented and there is no need to worry about the migration of the clot into the arterial system and the resulting complications.

The application of the thrombolytic agent 18 is followed by the injection of saline to flush the residual clot. This is followed by the application of a contrast material 22 through the second lumen 26 and the infusion apertures 12 to visualize the graft 42 and residual clots or stenosis, if any. The application of contrast material 22 can also be done after mechanical thrombectomy is performed with any known devices. As with the application of the thrombolytic agent 18, the contrast material 22 may be applied without worrying about the dislodgement of the clot 38 and migration of the dislodge clot 38 to the arterial system since the inflated distal balloon 16 is blocking entry of the dislodged clot 38 into the artery.

Once the graft is visualized using the contrast material 22, the inflated distal balloon 16 is pulled back toward the venous side 46, eradicating the arterial plug and removing the platelet plug and residual arterial anastomosis from the shunt-artery juncture. This can be repeated several times if needed. If necessary, direct injection of thrombolytic agent can be performed also towards the venous anastomosis.

The final step is that of removing the balloon, wire and the sheath.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for the treatment of thrombosed hemodlialysis access grafts or fistulas defining a shunt positioned between an arterial side and a venous side, comprising the following steps:
    inserting a balloon catheter within the shunt, the balloon catheter including a distal balloon and at least one infusion aperture located proximally of the distal balloon;
    advancing the balloon catheter within an arterial anastomosis at an artery-shunt juncture;
    inflating the distal balloon;
    injecting a thrombolytic agent through the at least one infusion aperture of the balloon catheter into the shunt to chemically destroy clot material within the shunt, wherein by applying the thrombolytic agent with the distal balloon inflated at the arterial anastomosis the possibility of the clot material moving into the artery is prevented and there is no need to worry about the migration of the clot into the arterial system and the resulting complications; and
    pulling the inflated distal balloon toward the venous side, eradicating the arterial plug.

2. The method according to claim 1, wherein, prior to inserting the balloon catheter, a dilatation catheter is advanced into a venous anastomosis and inflated to crush the venous anastomosis and open a shunt-vein juncture.

3. The method according to claim 2, wherein the step of advancing the dilatation catheter includes removing the dilatation catheter prior to insertion of the balloon catheter.

4. The method according to claim 2, wherein the step of injecting the thrombolytic agent includes spraying the thrombolytic agent with such force that the force of the spray created by the application of the thrombolytic agent mechanically disrupts the clot.

5. The method according to claim 4, wherein the step of injecting the thrombolytic agent is followed by the injection of saline to flush any residual clot material.

6. The method according to claim 5, wherein the step of injecting the thrombolytic agent is followed by applying a contrast material within the shunt and visualizing the shunt.

7. The method according to claim 6, wherein the step of pulling the inflated distal balloon includes removing a platelet plug and residual arterial anastomosis from the shunt-artery juncture.

8. The method according to claim 1, wherein the step of injecting the thrombolytic agent includes spraying the thrombolytic agent with such force that the force of the spray created by the application of the thrombolytic agent mechanically disrupts the clot.

9. The method according to claim 1, wherein the step of injecting the thrombolytic agent is followed by the injection of saline to flush any residual clot material.

10. The method according to claim 1, wherein the step of injecting the thrombolytic agent is followed by applying a contrast material within the shunt and visualizing the shunt.

11. The method according to claim 1, wherein the step of puffing the inflated distal balloon includes removing a platelet plug and residual arterial anastomosis from the shunt-artery juncture.

12. The method according to claim 1, wherein the step of inserting the balloon catheter includes inserting the balloon catheter into a clean shunt region.

* * * * *